United States Patent
Goto et al.

[11] Patent Number: 6,046,033
[45] Date of Patent: Apr. 4, 2000

[54] BASIC OSTEOBLAST GROWTH FACTOR II (BOGF-II)

[75] Inventors: Masaaki Goto; Eisuke Tsuda; Kazuki Yano; Fumie Kobayashi, all of Tochigi; Kyoji Yamaguchi, Saitama; Naohiro Washida, Tochigi; Masatsugu Ueda, Saitama; Tomonori Morinaga; Toshiko Satake, both of Tochigi; Kanji Higashio, Saitama, all of Japan

[73] Assignee: Snow Brand Milk Products Co., Ltd., Sapporo, Japan

[21] Appl. No.: 08/604,965

[22] PCT Filed: Jun. 26, 1995

[86] PCT No.: PCT/JP95/01270

§ 371 Date: Feb. 26, 1996

§ 102(e) Date: Feb. 26, 1996

[87] PCT Pub. No.: WO96/00240

PCT Pub. Date: Jan. 4, 1996

[30] Foreign Application Priority Data

Jun. 27, 1994 [JP] Japan .................................. 6-168984

[51] Int. Cl.[7] .......................... C07K 14/51; C07K 14/475
[52] U.S. Cl. .................... 435/69.4; 435/69.1; 435/252.3; 435/325; 530/300; 530/324; 530/350; 530/397; 530/399; 536/23.1; 536/23.5; 436/501
[58] Field of Search ..................................... 530/300, 324, 530/350, 399, 397; 536/23.1, 23.5; 435/240.2, 252.3, 69.1, 69.4, 325; 436/501

[56] References Cited

U.S. PATENT DOCUMENTS 5,200,509  4/1993  Spencer et al. ......................... 530/350

OTHER PUBLICATIONS

Reeck et al. Cell 50:667, 1987.

Bowie et al. Science 247:1306–1310, 1990.

Lewin. Science 237:1570, 1987.

Ngo et al. The Protein Folding Problem & Tertiary Structure Prediction, Merz et al, eds, Boston, 1994.

Wood et al. Mol. Endocrinol. 2:1176–1185, 1988.

Georges et al., pp. 127–149 in Macromolecular Sequencing and Synthesis: Selected Methods and Applications, ed. D. H. Schlesinger, Alan R. Liss, Inc., NY, 1988.

*Primary Examiner*—Elizabeth C. Kemmerer
*Attorney, Agent, or Firm*—Burgess, Ryan & Wayne

[57] ABSTRACT

A protein is provided derived from human fibroblast having an N-terminal amino acid sequence represented by SEQ ID NOS: 1 and 2, having a molecular weight of approximately 15kD under reducing and non-reducing conditions by (dosium dodecyl sulfate-polyacrylamide gel electrophoresis), and having an activity to stimulate growth of osteoblast. The protein is produced by gene engineering procedures, contains the amino acid sequence represented by SEQ ID NO: 9 and has osteoblast growth activity. Also provided is a method for preparing the protein by culturing human fibroblast and treating the conditioned medium for purification. The protein is utilized for the treatment of diseases characterized by decreased bone mass such as osteoporosis or is utilized as an antigen for immunological diagnosis of diseases.

5 Claims, 7 Drawing Sheets

BASIC OSTEOBLAST GROWTH FACTOR II (BOGF-II)

RELATED APPLICATION

This application is a national stage application of International (PCT) Application JP95/01270 filed Jun. 26, 1995.

FIELD OF THE INVENTION

This invention relates to a novel protein, basic osteoblast growth factor II (bOGF-II) which stimulates osteoblast growth, and methods for producing the protein.

BACKGROUND ART

Human bones are always remodelling by the repeated process of resorption and reconstitution. In the process, osteoblasts and osteoclasts are considered to be the calls mainly in charge of bone formation and bone resorption, respectively. A typical example of disease caused by abnormal bone metabolism proceeded by the bone cells is osteoporosis. The disease is known to be provoked by the condition in which bone resorption by osteoclasts exceeds bone formation by osteoblasts, but the mechanism of osteoporosis has not yet been completely elucidated. Osteoporosis causes pain in the bone and makes the bone fragile, leading to fracture. Since osteoporosis increases the number of bedridden old people, it has become a social issue with the increasing number of old people. Therefore, efficacious drugs for the treatment of the disease are expected to be developed. Bone mass reduction caused by the abnormal bone metabolism is thought to be treated by inhibiting bone resorption, improving bone formation, or improving the balanced metabolism.

Bone formation is expected to be promoted by stimulating growth, differentiation, or activation of osteoblasts. Recently, cytokines which stimulates growth or differentiation of osteoblasts have been attracted public attention and have been intensively studied. Many cytokines are reported to stimulate the growth of osteoblasts, i.e. fibroblast growth factor (FGF) (Rodan S. B. at al., Endocrinology vol.121, p1917, 1987), insulin-like growth f actor-I (IGF-I) (Hock J. M. et al., Endocrinology vol. 122, p254, 1988), insulin-like growth factor-II (IGF-II) (McCarthy T. et al., Endocrinology vol.124, p301, 1989), and bone morphogenetic protein (BMP) (Sampath T.K. etl al., J. Biol Chem. vol.267, p20532, 1992, Knutsen R. et al., Biochem. Biophys. Res. Commun. vol.194, p1352, 1993, and Akira Yamaguchi et al., Zikken Igaku vol.10, p2003, 1992). Many cytokines are also reported to stimulate the differentiation of osteoblasts, i.e. transforming growth factor-s (TGF-P) (Centrella M. et al., J. Biol. Chem. vol.262, p2869, 1987), insulin-like growth factor (IGF), and bone morphogenetic protein (Takuwa :Y. et al., Biochem. Biophys. Res. Commun. vol.174, p96, 1991, and Knutsen R. et al., Biochem. Biophys. Res. Commun. vol.194, p1352, 1993). These cytokines are expected to be efficacious drugs for improving bone mass by stimulating bone formation; some of the cytokines such as bone morphogenetic proteins are now investigated in clinical trials for their effects to cure the patients with bone diseases.

Examples of drug products now clinically utilized for the treatment of bone diseases and for shortening the treatment period are dihydroxy vitamine $D_3$, calcitonin and its derivatives, hormones such as estradiol, lprif lavon, and calcium preparations. However, these drug products do not provide satisfactory therapeutic effects, and novel drug substances have been expected to be developed. As mentioned, bone metabolism is controlled in the balance between bone resorption and bone formation. Therefore, cytokines which stimulate osteoblast growth and osteogenesis are expected to be developed as drug for the treatment of bone diseases such as osteoporosis.

Disclosure of the Invention

The inventors have intensively searched for osteoblast growth factors, and have found a novel osteoblast growth factor. The inventors have also established methods for accumulating the protein in a high concentration and purifying it efficiently.

A cDNA clone encoding this protein was isolated by using the partial amino-acid sequences of the native bOGF-II protein. Moreover, bOGF-II was produced by the genetic engineering techniques with this cDNA. The object of the invention is to provide a novel osteoblast growth factor. (protein) and methods for efficiently producing the protein.

The inventors screened animal cells conditioned media, and have found the osteoblast growth factor in human fibroblast IMR-90 (ATCC-CCL186) conditioned medium. The inventors examined the culture conditions of IMR-90 cells, and have established the method for culturing the cells on alumina ceramic fragments to accumulate the osteoblast growth factor in a high concentration in the culture medium. The inventors found the method to purify bOGF-Il efficiently by a combination of ion-exchange column and/or heparin column.

Moreover, the inventors determined the amino acid sequences of the bOGF-II protein, designed the primers based on these amino acid sequences, and obtained a cDNA fragments of bOGF-II from a cDNA library of IMR-90 cells.

A cDNA clone encoding the full length protein of the current invention was isolated from a cDNA library of IMR-90 cells by hybridization using the cDNA fragment as a probe. Furthermore, the inventors established a method for producing recombinant bOGF-II in the culture media of the cells which was transformed by expression vector containing the cDNA.

This invention relates to a protein characterized by the following features: (1) derived from human fibroblast cells, (2) molecular weight of ca. 15kD on sodium dodecyl sulfate polyacrylamide gel electrophoresis (SDS-PAGE) under reducing and non-reducing conditions, (3) a high affinity for cation exchanger and heparin, (4) decrease in osteoblast growth activity by heating at 70° C. for 10 minutes, and (5) inactivation by heating at 90° C. for 10 minutes. bOGF-II in the present invention is apparently different from known osteoblast growth factors in N-terminal amino acid sequence. The N-terminal amino acid sequences of bOGF-II are shown in Sequence Number 1 and 2.

The invention also relates to a method for producing bOGF-II, comprising: (1) culturing human fibroblasts, (2) treating the culture medium through a heparin-column, (3) eluting an adsorbent fraction, (4) treating the eluate through an anion-exchange column to obtain a non-adsorbent fraction, (5) applying the fraction to a cation-exchange column, and (6) purifying the objective protein through a heparin-column.

Purification procedure according to the invention includes any means having the same effect as that obtained by the method for mixing a culture medium with heparin-Sepharose, etc. in a batchwise operation and for treating through a column, as well as a simple method for flowing a culture medium through heparinSepharose column, etc.

bOGF-II can be efficiently isolated from a culture medium of human fibroblasts at a high yield according to the invention. Isolation of bOGF-II is based on general means for purifying proteins from biomaterials, utilizing physical and chemical properties of the objective protein bOGF-II. For example, concentration procedure includes general biochemical technique such as ultrafiltration, lyophilization, and dialysis. Purification procedure includes combinations of several technique for purifying proteins, such as ion-exchange chromatography, affinity chromatography, gel filtration chromatography, hydrophobic chromatography, reversed-phase chromatography, and preparative gel electrophoresis. Human fibroblast is preferably IMR-90. The culture medium of human fibroblast cell IMR-90 is obtained by absorbing human fibroblast cell IMR-90 on ceramic, and culturing in DMEM medium supplemented with 5% fetal calf serum in a roller bottle in stationary state for about a week. For purification, 0.1% CHAPS (3-[(3-cholamidopropyl)-dimethylammonio]-1-propane sulfonate) is preferably added to a buffer as surfactant.

The protein of the invention is purified by applying the culture medium to a heparin-column (heparin-Sepharose CL6B, manufactured by Pharmacia), eluting with 10 mM Tris-HCl buffer containing 2 M NaCl, pH 7.5 applying the diluted fraction to anion-exchange column (Hiload-Q/FF, manufactured by Pharmacia), collecting an non-adsorbent fraction, and applying the obtained fraction to S cation-exchange column (Hiload-S/HP, manufactured by Pharmacia) to fractionate three peaks, bOGF-I (0.15 M NaCl), bOGF-II (0.35 M NaCl), and -bOGF-III (0.55 M NaCl) in the order that the activity is eluted in lower concentrations of NaCl. bOGF-II can be isolated by the following repeated heparin column chromatography (heparin-5PW, manufactured by Toso Co.), and can be identified by the previously described properties. It is likely that the protein bOGF-III is basic fibroblast growth factor from the results that it is inactivated by heating at 70° C. for 10 minutes, it is eluted by ca. 1.8 M NaCl from heparin 5PW column, and it is inactivated by anti-basic fibroblast growth factor antibody.

Furthermore, a method for producing recombinant bOGF-II was established. The method includes the following three steps; First, amino-acid sequences of bOGF-II are used to design oligonucleotide primers. Second, a bOGF-II cDNA fragment is obtained by PCR amplification using the primers. Finally, the cDNA clone encoding the full length bOGF-II is isolated from a cDNA library of IMR-90 cells by hybridization using the cDNA fragment as a probe. Moreover, bOGF-II is recovered and purified from culture medium or the cells by culturing host cells selected from eukaryote such as mammalian cells (e.g. chinese hamster ovary cell) or prokaryote such as bacteria (e.g. *E. coli.*), which are transfected by vector, having expression promoter and the cDNA coded full-length bOGF-II.

The invention relates to proteins having an activity to stimulate growth of osteoblasts, containing the described amino acid sequence as a part, or having a homology with the described amino acid sequence more than 801, and cDNA of the protein.

OGF activity can be evaluated by utilizing osteoblastic cell lines or normal asteoblasts as target cells and by measuring an increased incorporation $^3$H-thymidine to the cells. The target cell is preferably mouse osteoblastic cell line MC3T3-E1 (J. Oral. Bio. Cell. Biol. 96, 191, 1983). The cell is reported to be responsive to vitamin $D_3$ and parathyroid hormone and to grow up to be calcificated in vitro in a manner similar $_{to}$ that in vivo. The OGF activity is preferably measured with a serum-free medium, and can be exactly evaluated at high sensitivity by measuring incorporation of $^3$H-thymidine.

bOGF-II is useful as a pharmaceutical composition for treating or improving decreased bone mass such as in osteoporosis and other diseases with abnormal bone metabolism, or as antigen for immunological diagnosis of the diseases.

bOGF-II is formulated to be pharmaceutical preparation, and can be orally or parenterally administered. The preparation comprises bOGF-II as a an effective ingredient, and is safely administered to human beings. Examples of the pharmaceutical preparation include compositions for injection or intravenous drip, suppositories, nasal preparations, sublingual preparations, and tapes for percutaneous absorption. The preparation for injection is a mixture of bOGF-II in pharmacological effective amount and pharmaceutically-acceptable carrier. The carrier is vehicle/activator which is generally added to compositions for injection, e.g. amino acids, saccharides, cellulose derivatives, and other organic/inorganic compounds. When mixing bOGF-II with the vehicle/activator to prepare injections, pH adjustor, buffer, stabilizer, solubilizing agent, etc. may be added as needed.

Figure 3:
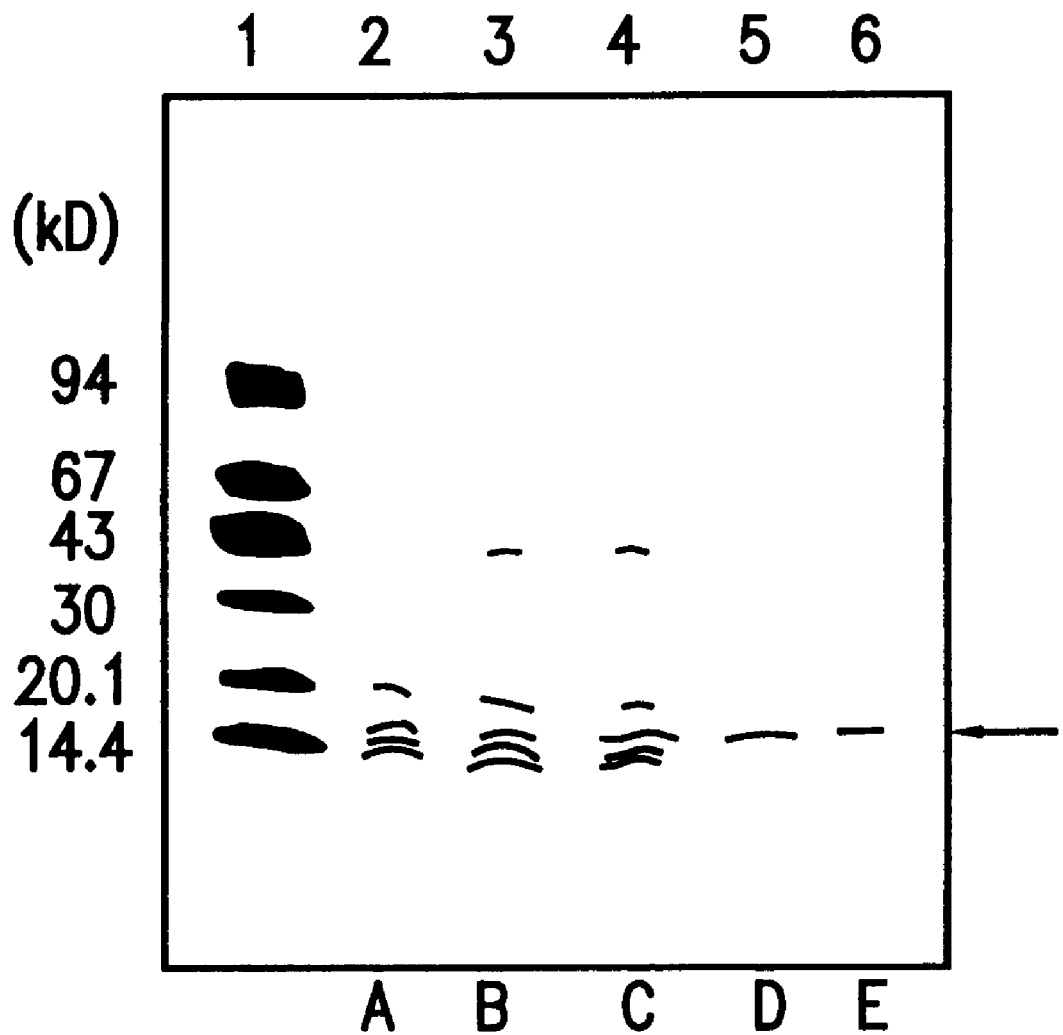
FIG. 3 shows pattern of bOGF-II on sodium dodecyl sulfate-polyacrylamide gel electrophoresis (SDS-PAGE) under non-reducing condition.

In the FIG. 3, lane 1 indicates molecular weight marker, lane 2 indicates fraction A, lane indictes fracton B, lane 4 indicates fraction C, lane 5 indicates fraction D, and lane 6 indicates fraction E.

Figure 2:
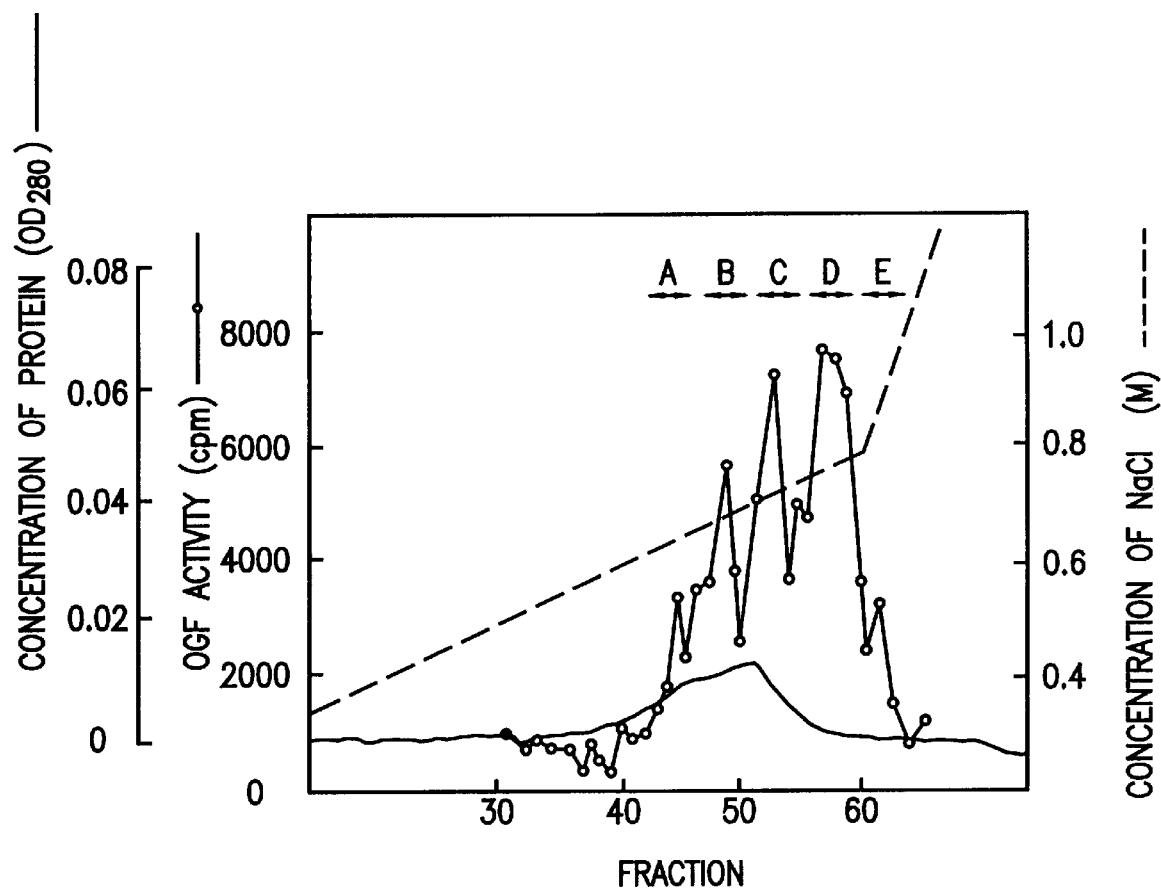
FIG. 2 shows elution pattern of bOGF-II fraction on an affinity column (Heparin 5PW TM, 0.8×7.5 cm, manufactured by Toso Co.).

See FIG. 2 for the fractions A–E.

Figure 4:
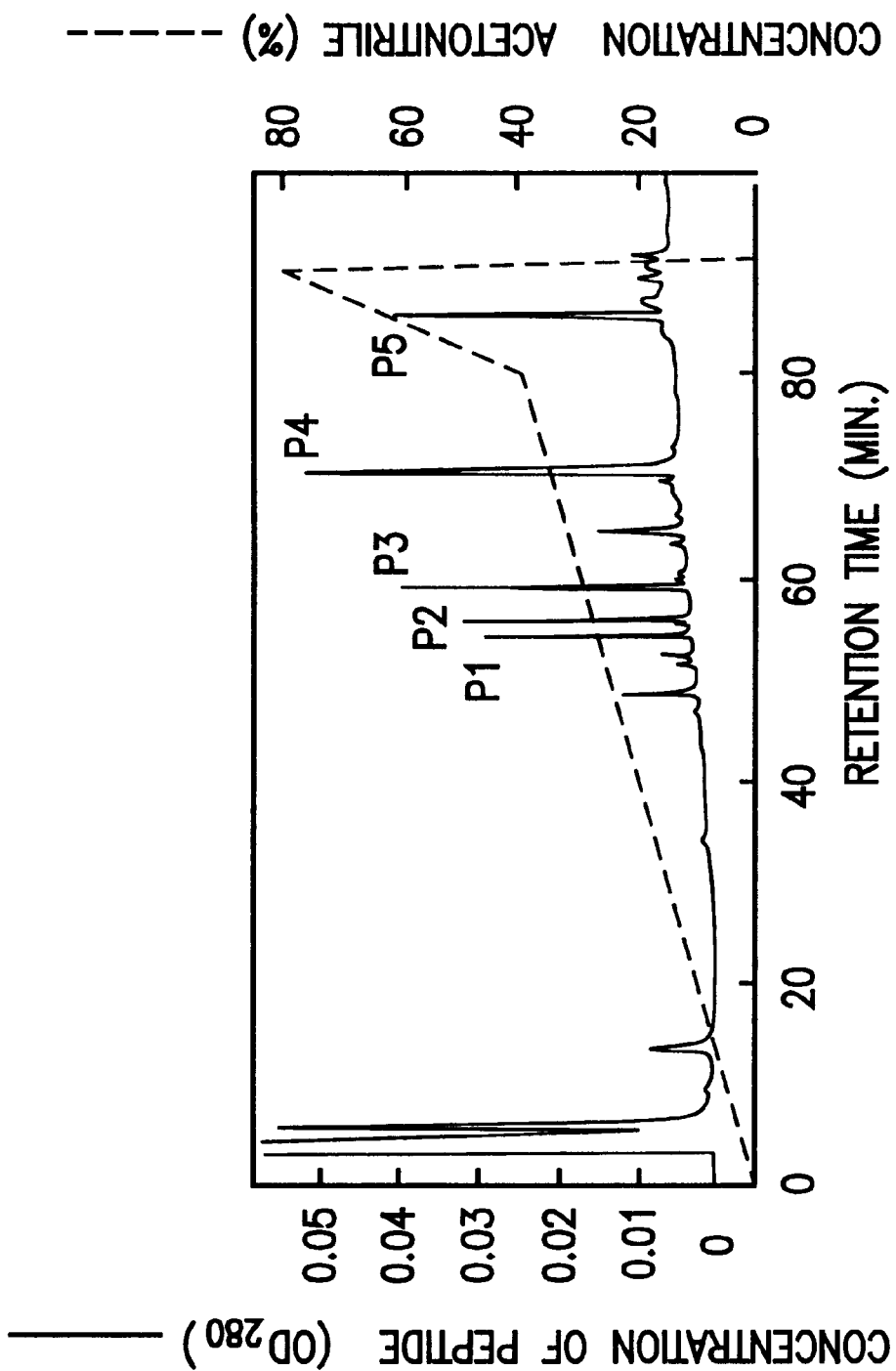

FIG. 4 shows elution pattern of the peptides from reduced PE bOGF-II which was digested with endoproteinase Asp-N (manufactured by Bayringer Co.) on a reversed-phase column (OD-300, C18, 2.1×200 mm, manufactured by Applied Biosystems Co.).

Figure 5:
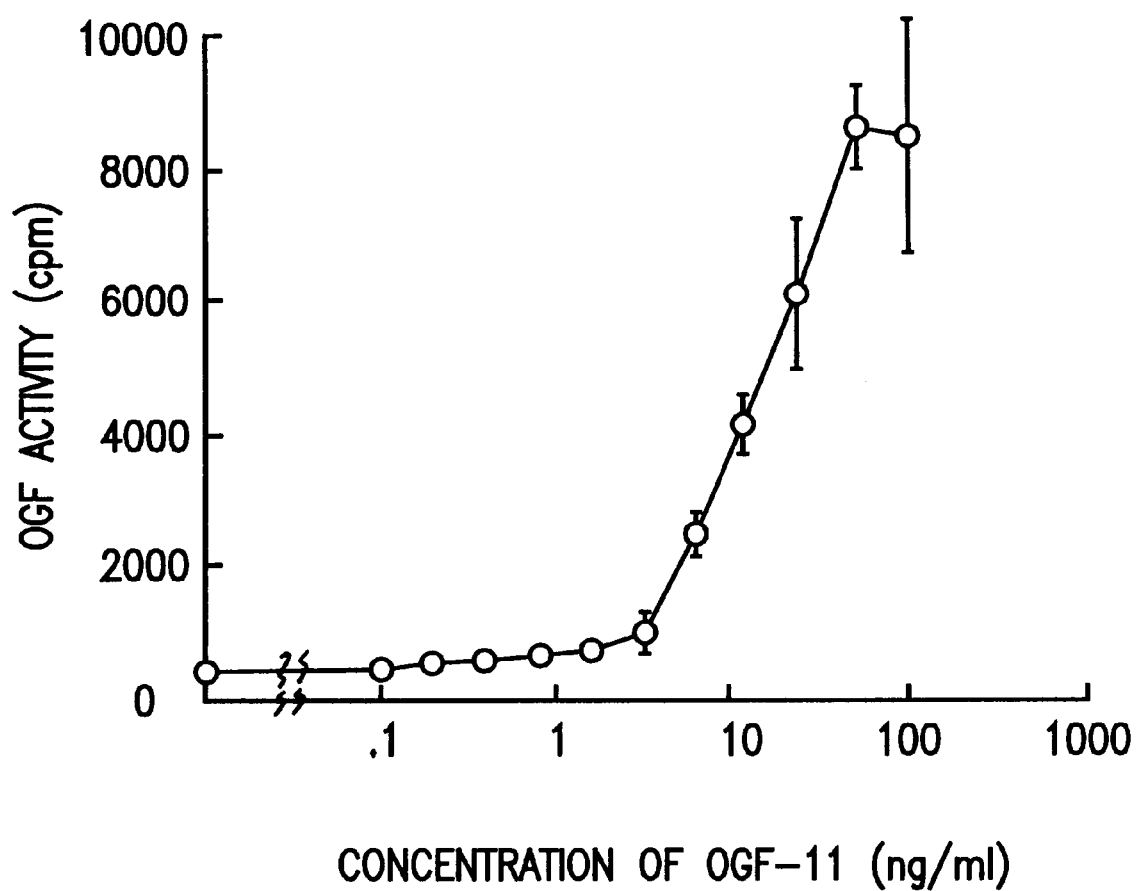

FIG. 5 shows activity of bOGF-II tested with MC3T3-E1.

Figure 6:
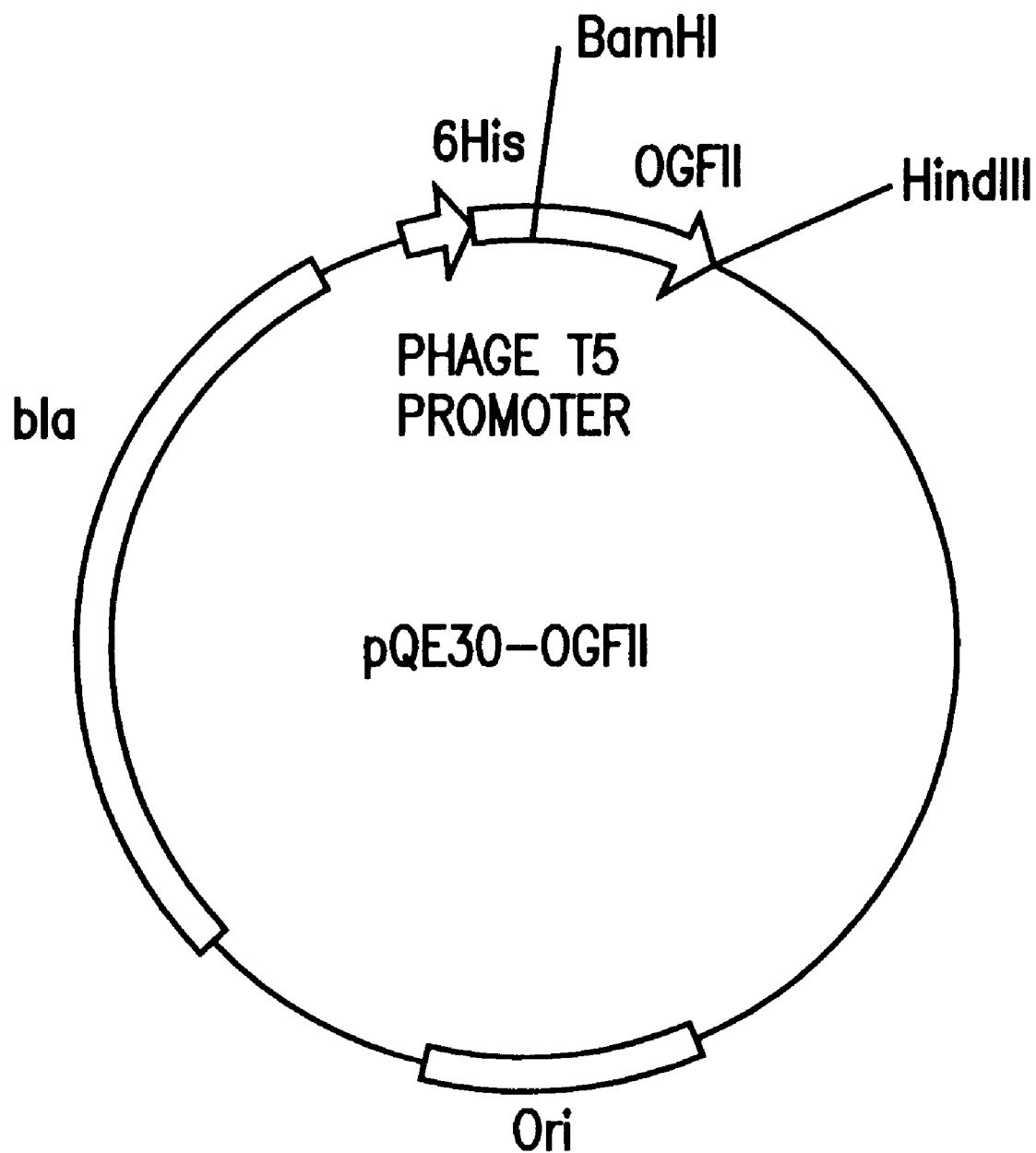

FIG. 6 shows the structure of plasmid pQE30-OGF-II. In this drawing, 6His represents histidine cluster; Phage T5 promoter represents phage T5 promoter; bla represents an ampicillin resistant gene; Ori represents-replication origin in *E. coli* and bOGF-II represents OGF-II cDNA, respectively.

Figure 7:
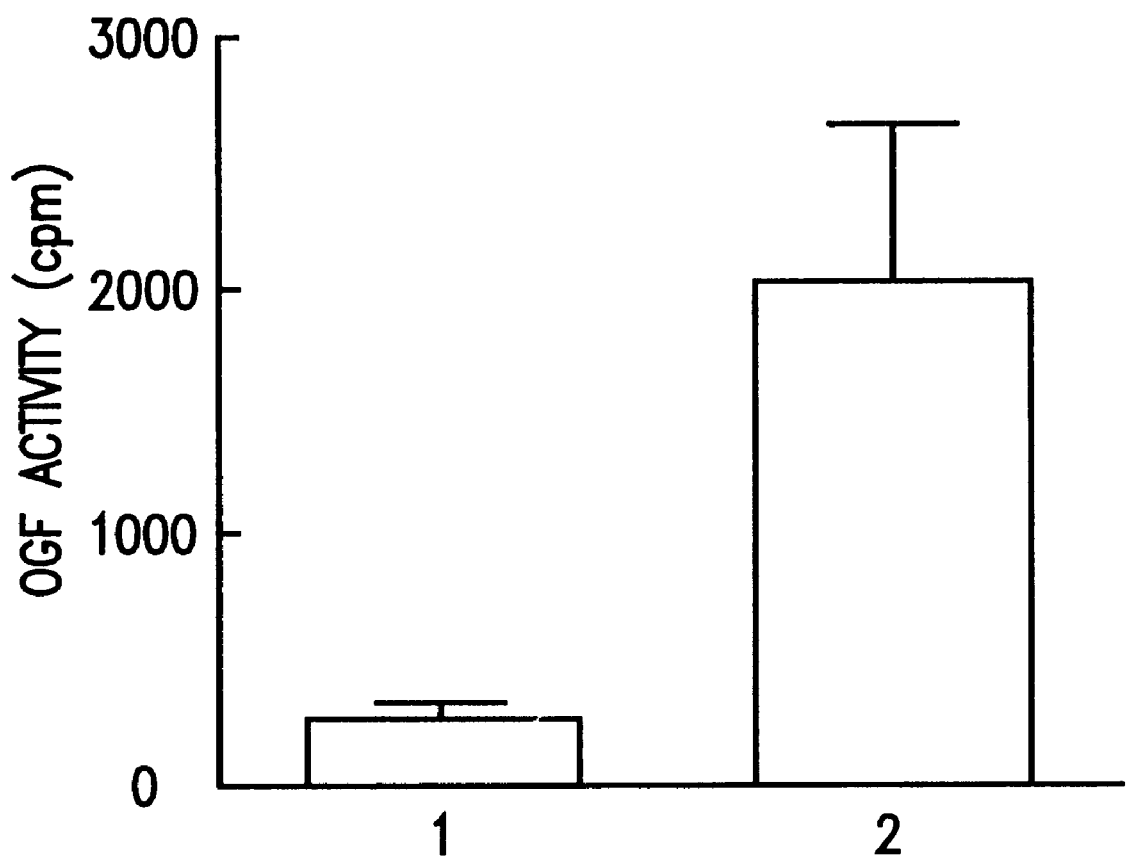

FIG. 7 shows activity of His6-bOGF-II tested with MC3T3-E1.

In the drawing, column 1 shows a control and column 2 shows the activity when a 10% solution of Hls6-bOGF-II is added.

THE BEST MODE TO CONDUCT THE INVENTION

[Examples]

Detailed description of the invention is provided by way of examples as follows. However, it should be noted that the examples are simply illustrative, and the invention is not restricted to them.

Example 1 Production of natural type of bOGF-II
(1) Preparation of a conditioned medium of human fibroblast IMR-90

Human fetal lung fibroblast IMR-90 (ATCC-CCL186) was cultured on alumina ceramic fragments (80 g) (alumina: 99.5%, manufactured by Toshiba Ceramic K.K.) in DMEM medium (manufactured by Gibco Co.) supplemented with 5% FCS and 10 mM HEPES buffer (500 ml/roller bottle) in stationary state at 37° C. in the presence of 5% $CO_2$ for 7 to 10 days using 60 roller bottles (490 $cm^2$, 110×171 mm, manufactured by Coning Co.). The conditioned medium was harvested, and a fresh medium was added to obtain 30L of IMR-90 conditioned medium in one batch of culture. The obtained conditioned medium was designated as sample 1.

(2) A method for testing osteoblast growth activity

Activity of osteoblast growth factor was evaluated by measuring DNA incorporation to mouse osteoblast MC3T3-E1 (granted by Dr. Masayoshi Kumegawa, Professor of the Department of Dentistry at Meikai University). Precisely, sample solution (50 $\mu$l) which was diluted with α-MEM medium (manufactured by Gibco Co.) containing no nucleic acids and supplemented with 0.2% BSA, was transferred to a 96-well microplate. Next, MC3T3-El cells in the α-MEM medium were inoculated to the microplate at $2×10^3$ cells/50 $\mu$l and were cultured at 37° C. in 5% $CO_2$ air for 15 to 20 hours. After the culture, 10 $\mu$l of $^3$H-thymidine (TRK686, manufactured by Amasham Co.) diluted with phosphate buffered saline to 0.1mCi/ml was added to the each wells. After two hours, radioactivity of $^3$H-thymidine incorporated into the cells was measured by a Matrix A counter (manufactured by Packard Co.).

(3) Purification of bOGF-II i) purification on heparin Sepharose CL-62

The IMR-90 conditioned medium (ca. 90L) sample 1) was filtrated with 0.22 $\mu$m membrane filter (hydrophilic Milidisk, 2000 $cm^2$, manufactured by Milipore Co.), and was divided into three fractions. Each fraction was applied to haparin Sepharose CL-6B (5×4.1 cm) (80 ml) equilibrated with 10 mM Trls-HCI 0.3 M NaCl pH 7.5. After washing with tomM Triso-HCl, pH 7.5 at a flow rate of 500 ml/hr., a heparin Sepharose CL-6B adsorbent protein fraction was eluted with l-mM Tris-HCu, 2M NaCl, pH 7.5. This fraction was designated as sample 2.

ii) purificatin on HiLoad-Q/FF

The heparin Sepharose adsorbent fraction (sample 2) was dialyzed against 10 mM Tris-HCl, pH 7.5, supplemented with CHAPS to the final concentration of 0.1%, incubated at 4° C. overnight, and divided into two fractions. Each fraction was then applied to an anion-exchange column (HiLoad-Q/FF, 2.6×10 cm, manufactured by Pharmacia Co.) equilibrated with 50mM Tris-HCl, 0.1% CHAPS, pH 7.5 to obtain a non-adsorbent fraction (1000 ml). This fraction was designated as sample 3.

iii) purification on HiLoad-S/HP

Figure 1:
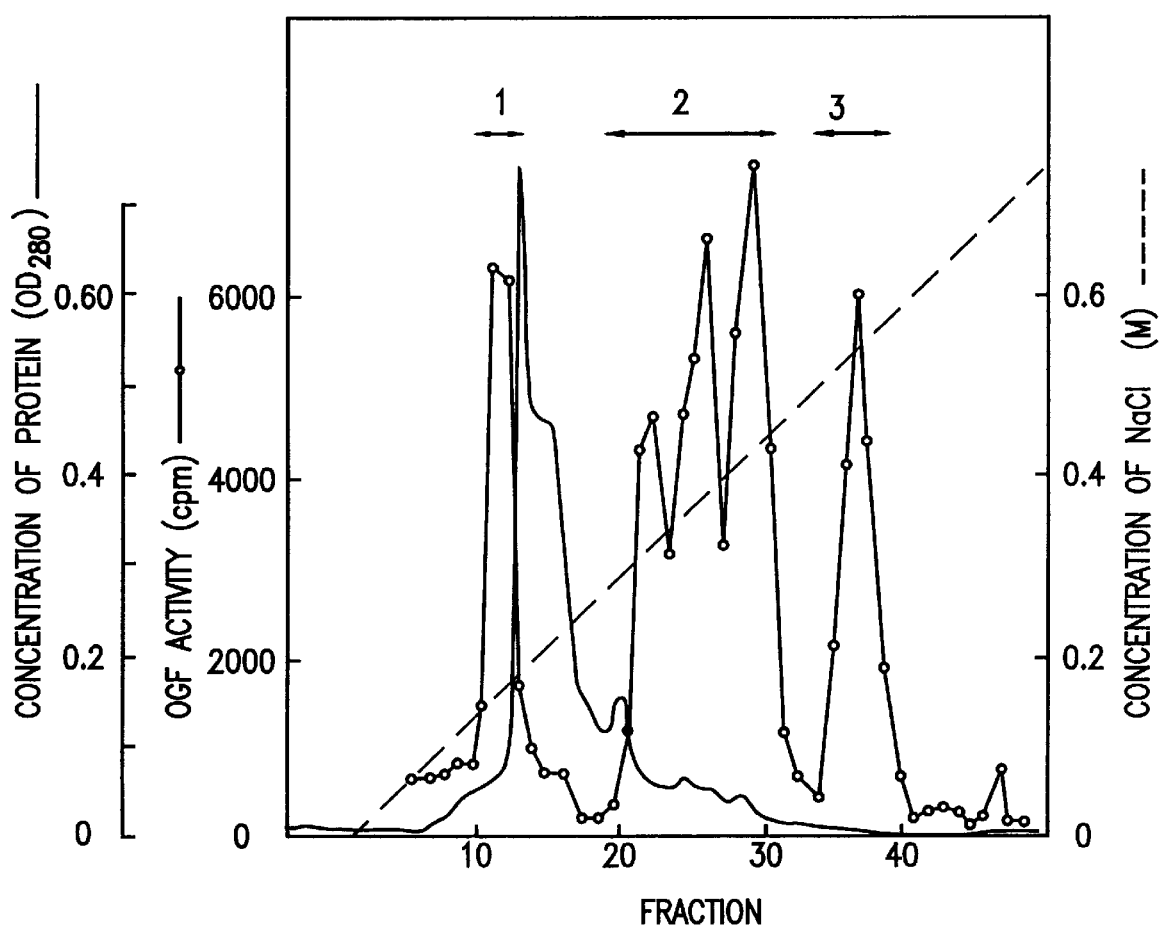
FIG. 1 shows elution pattern of bOGF fractions on a cation-exchange column (HiLoad-S/HP™, 2.6×10 cm, manufactured by Pharmacia Co.). In the FIG. 1, peak 1 indicates bOGF-I, peak 2 indicates bOGF-II, and peak 3 indicates bOGF-III.

The HiLoad-Q non-adsorbent fraction (sample 3) was applied to a cation-exchange column (HiLoad-S/HP, 2.6×10 cm, manufactured by Pharmacia Co.) equilibrated with 50 mM Tris-HCl, 0.1% CHAPS, pH 7.5. After washing with 50 mM Tris-HCl, 0.1% CHAPS, pH 7.5, the adsorbed protein was eluted with 0–1M NaCl on a linear gradient over 100 minutes at a flow rate of 8 ml/min. The eluate was fractionated at 12 ml/fraction. Each fraction (10 $\mu$l) was evaluated for OGF activity according to the method in (2). OGF adtivity was found in three peaks (peak 1: bOGF-I, peak 2: bOGF-II, peak 3: bOGF-III). The result was shown in FIG. 1.

The peak 3 was supposed to be bFGF from the fact that OGF activity in peak 3 was inactivated by heating at 70° C. for 10 minutes, was eluted with ca. 1.8 M NaCl from heparin column, and was neutralized by anti-human bFGF antibody.

iv) purification on affinity column (heparin-5PW)

The peak 2 (bOGF-II) fraction (120 ml) was diluted with 240 ml of 50 mM Tris-HCl, 0.14 CHAPS, pH 7.5, and applied to an affinity column (heparin-5PW, 0.8×7.5 cm, manufactured by Toso Co.) equilibrated with 50 mM Tris-HCl, 0.1% CHAPS, pH 7.5. After washing with 50 mM Tris-HCl, 0.1% CHAPS, pH 7.5, the adsorbed protein was eluted with 0–2 M NaCl on a linear gradient over 60 minutes at a flow rate of 0.5 ml/min. The eluate was fractionated at 0.5 ml/fraction. Each fraction (2 $\mu$l) was eveluted for OGF activity. A fraction (5 ml) eluted with ca. 1.0–1.2 M NaCl was found to have OGF activity and designated as sample 4.

The sample 4 (5 ml) was diluted with 10 ml of 50 mM Tris-HCl, 0.1 % CHAPS, pH7.5, and applied to an affinity column (heparin-5PW, 0.8×7.5 cm, manufactured by Toso Co.) equilibrated with 50 mM Tris-$HCl_1$, 0.1% CHAPS, pH 7.5. After washing with 50 mM Tris-HCl, 0.1% CHAPS, pH 7.5, the adsorbed protein was eluted with 0–2 M NaCl on a linear gradient at a flow rate of 0.5 ml/min. The eluate was fractionated at 0.5 ml/fraction. Each fraction (2 $\mu$l) was evaluated for OGF activity. A fraction (5 ml) eluted with ca. 1.0–1.2M NaCl was found to have OGF activity and was designated as sample 5.

The sample 5 (5 ml) was diluted with 10 ml of 50 mM Tris-HCl, 0.1% CHAPS, pH 7.5, and applied to an affinity column (heparin-5PW, 0.5×7.5 cm, manufactured by Toso Co.) equilibrated with 50 mM Tris-HCl, 0.1% CHAPS, pH 7.5. After washing with 50 mM Tris-HCl, 0.2 M NaCl, 0.1% CHAPS, pH 7.5, the adsorbed protein was eluted with 0.2–0.8 M NaCl on a linear gradient over 60 minutes at a flow rate of 0.5 ml/min. The e.uate was fractionated at 0.5 ml/fraction. Each fraction (4 $\mu$l) was evaluated for OGF activity. The result was shown in FIG. 2.

(4) Molecular weight of bOGF-II

The obtained OGF fraction was divided into five fractions at 2 ml/fraction (FIG. 2, fractions A-E). Each fraction (100 $\mu$l) was subjected to SDS-polyacrylamide gel electrophoresis under non-reducing condition. Precisely, each of the fractions A-E (100 $\mu$l) was dialyzed against water, lyophilized, dissolved in 1.5 $\mu$l of a mixture of 10 mM Tris-HCl, pH8, 1 mM EDTA, 2.5% SDS, 0.01% bromophenol blue, and incubated at 37° C. overnight. The 1 $\mu$l of sample was then analyzed by SDS-polyacrylamide gel electrophoresis with a gradient gel of 8–25% acrylamide (manufactured by Pharmacia Co.) and an electrophoresis device (Fast System, manufactured by Pharmacia Co.). The following molecular weight markers were utilized: phospholipase b (94kD), serum albumin (67kD), ovalbumin (43kD), carbonic anhydrase (30kD), trypsin inhibitor (20.1kD), and a-lactoalbumin (14.4kD). After electrophoresis, protein bands were visualized by silver stain according to a protocol of Pharmacia Co.. The result was shown in FIG. 3.

Protein band detected at molecular mass of 15kD, was proportional to OGF activity. The fractions D and E contained only the protein band at 15kD. When this protein was analyzed by SDS-polyacrylamide gel electrophoresis under reducing condition, a single protein band was detected at almost the same molecular weight as that obtained under non-reducing condition.

(5) Determination of N-terminal amino acid sequence

The obtained fraction D (500 $\mu$l) was applied to a reversed-phase column (BU-300, C4, 2.1×220 mm, manufactured by Applied Biosystems Co.) equilibrated with a mixture of 0.1% luoroacetic acid (TFA), 10% acetonitrile, and eluted on a linear gradient of 10–60% acetonitrile over 50 minutes at a flow rate of 0.2 ml/min., to obtain the desalted and concentrated sample. This sample was analyzed by protein sequencer (477A-120A, manufactured by Applied Biosystems Co.) for N-terminal amino acid sequence. The amino acid sequence of the obtained peptide is shown in SEQ ID NO:1. In the sequence, —Xaa— indicates an amino acid not yet identified.

(6) Determination of protein amino acid sequence

The fraction C (2000 μl) was concentrated, dissolved with 300 μl of 0.5 M Tris-HCl, pH8.5 containing 10 mM EDTA, 7 M guanidine hydrochloride, and dithiothreitol (1 mg), incubated at room temperature for four hours, further supplemented with 2 μl of 4-vinylpyridine, and left in the darkness at room temperature overnight for pyridylethylation (PE). To the sample, 3 μl of 25% TFA was added. The mixture was then applied to a reversed-phase column (BU-300, C4, 4.6×30 mm, manufactured by Applied Biosystems Co.) equilibrated with 10% acetonitrile containing 0.1% TFA, and eluted with 10–50% acetonitrile on a linear gradient over 50 minutes at a flow rate of 1 ml/mln. to obtain reduced PE bOGF-II. A quarter of the obtained reduced PE bOGF-II was an alyzed by protein sequencer (477A-120A, manufactured by Applied Biosystems Co.) for N-terminal amino acid sequence. The obtained amino acid sequence of the peptide is shown in SEQ ID NO. 2.

The residual three quarters of the reduced PE bOGF-II were digested with 0.5 μl of endoproteinase Asp-N (manufactured by Boehringer Mannheim Co.) in a mixture (50 μl) of 50 mM phosphate buffer, pH 8.5 containing 1M urea at 37° C. for 15 hours, applied to a reversed-phase column (OD-300, C18, 2.1×220 mm, manufactured by Applied Biosystems Co.) equilibrated with 0.1% TFA, and eluted on a linear gradient of 0–40% acetonitrile over 80 minutes at a flow rate of 0.2 ml/min.. Elution pattern is shown in FIG. 4. Detected five peaks were analyzed by protein sequencer (477A-120A, manufactured by Applied Biosystems Co.) for N-terminal amino acid sequence. Each amino acid sequence of the obtained five peptides is shown in SEQ ID NOS:3–7.

(7) Efficacy of byGF-II on the proliferation of MC3T3-El cells.

The fraction D was evaluated for protein concentration according to Lowry method by utilizing BSA (bovine serum albumin) as a standard. This sample was diluted to 100 ng/ml and evaluated for OGF activity, with two-fold intervals between contiguous doses, according to the method described in (2). The result is shown in FIG. 5.

Example 2. Preparation of bOGF-II by application of genetic engineering (1) Cloning bOGF-II gene (1) Cloning bOGF-II gene cDNA by PCR A set of primers for amplifying the tDNA were prepared on the basis of determined amino acid sequence of OGF-II. That is, from Glu-Thr-Glu-Tyr-Gly-Pro-Cys, (SEQ ID NO:15) an N-terminal amino acid sequence, the DNA sequence coding this was deduced, and mixed primers having the sequence of 51-GA(A/G)ACNGA(A/G)TA(T/C) GGNCCNTG-3' (SEQ ID NO:16) were synthesized. Here, A/G means A or G; T/C means T or C; and N represents A, G. C or T. From Asp-Lys-Lys-Gly-Phe-Tyr-Lys, (SEQ ID NO:11) an internal amino acid sequence, a DNA sequence coding this was deduced, and mixed primers having the complementary sequence chain of 5'-TT(A/G)TA(A/G) AANCC(T/C)TT(T/C)TT(A/G)TC-3' (SEQ ID NO:17) were synthesized. For the synthesis of the primers, DNA Synthesizer 394 of Perkin Elmer Co. was used. The two kinds of primers (200 pmol respectively) and single-stranded CDNA derived from Human fetal lung fibroblast IMR-90 polya RNA (1 μg) as the template DNA were used for the polymerase chain reaction (PCR). The enzyme used was EX Taq (manufactured by Takara Shuzo Co., Ltd.) The reaction solution contained 5 μl of 10×ExTaq buffer, 4 μl of 2.5 mM DNTP, 1 μl of the CDNA solution, 0.25 μl of Ex Taq, 29.75 μl of distilled water, and each 5 μl of the primer (40 μM) in a final volume of 50 μl. The reaction condition is as follows. After keeping the reaction mix at 95° C. for 3 minutes, 30 cycles of three-step incubation were performed that consisted of 95° C. for 3 minutes, 50° C. for 30 seconds, and 70° C. for 2 minutes. After these reactions, the reaction mix was kept at 70° C. for 5 minutes. After the reaction was completed, 8 μl of the reaction solution was subjected to 4% agarose gel electrophoresis; several bands including about 120 bp fragment were detected. The reaction solution in a volume of 4.5 μl, PCRII (original TA cloning kit, Manufactured by Invitrogen Co.) cloning vector in a volume of 0.5 μl, and DNA ligation kit (version 2) liquid 1 (manufactured by Takara Shuzo Co. Ltd.) in a volume of 5 μl were mixed and kept at 16° C. overnight. Using 5 μl of the ligation reaction solution, *E. coli* DH5α (prepared by BRL Co.) was allowed to transformation. The length of fragments inserted in the plasmid harbored inserted in the resultant ampicillin resistance bacteria was measured by PCR, and 4 strains having about 120 bp inserted fragment were isolated. In the reaction, the two kinds of primers mentioned above were used. From the 4 isolated strains, plasmid DNA was purified, and the DNA sequences of the inserted fragments were determined. When the amino acid sequence deduced from the nucleotide sequence was analyzed, all the clones had a reading frame that coincided with the amino acid sequence determined from OGF-II protein. One clone (Clone #1) was subjected to the following experiment.

(2) Cloning OGF-II full length CDNA

The plasmid of Clone #1 was purified, digested by a restriction enzyme EcoRI (Prepared by Takara Shuzo Co. Ltd.), and subjected to agarose gel electrophoresis, and OGF-II CDNA of about 120 bp was isolated. This fragment was labeled with $^{32}$P using Megaprime kit (manufactured by Amersham Co.).and α$^{32}$P-dCTP and served as the probe in the following experiment. From Human fetal lung fibroblast IMR-90 polyA$^+$ RNA (5 μg), double-stranded cDNA was-synthesized according to the manual of Great Lengths cDNA Synthesis kit (manufactured by Clontech Co.). The polyA$^+$ RNA was prepared by Fast Track (manufactured by Stratagene Co.). The method for synthesizing the double-stranded CDNA is briefly described below. The polyA$^+$ RNA (5 μg) and Oligo (dT)$_{25}$ (dN) primer were mixed and made into a final volume of 12.5 μl with addition of distilled water, and the solution was kept at 70° C. for 3 minutes and allowed to cool in ice for 2 minutes. Into this solution, 3.2 μl of distilled water, 5 μl of 5×First-strand buffer, 0.5 μl of DTT (dithiothreitol), 1.3 μl of dNTP (20 mM each) and 2.5 μl (500 units) of MMLV (RNaseH$^-$) were added, and the mixture was kept at 42° C. Further, 123.5 μl of distilled water, 40 μl of 5×second-strand buffer, 1.5 μl of dNTP (20 mM each) and 10 μl of Second-strand enzyme cocktail were added therein, and the mixture was kept at 16° C. for 2 hours. Into this reaction solution, 15 units of T4 polymerase was added; the resultant was kept at 16° C. for further 30 minutes and the reaction was stopped with addition of 10 μl of 0.2 M EDTA followed by chloroform and isoamyl alcohol treatments and ethanol precipitation. To the terminal of this double-stranded cDNA, EcoRI-SalI-NotI linker (prepared by Clontech Co.) was attached. Then, the resultant was inserted into ZAP Express phage (prepared by Stratagene Co.) DNA that was preliminarily cut with a restriction enzyme EcoRI and treated with CIAP (bovine tetis alkaline phosphatase). The recombinant DNA obtained was subjected to packaging, and infected to *E. coli* XL1-Blue MRF' (prepared by Stratagene Co.); plaques were formed on NZY agar medium (0.5% NaCl, 0.2% MgSO$_4$·7H$_2$O, 0.5% Yeast Extract, 1% NZ amine, pH 7.5, 1.5% agar). For the packaging, Gigapack II Gold packaging extract (prepared by Stratagene Co.) was used. The phage formed on the agar medium was -transferred onto nylon membrane, Hybond-N (manufactured by Amersham Co.) and the phage DNA was fixed. The resultant membrane was immersed into hybridization buffer that contained 100 μg/mL of salmon sperm DNA (manufactured by Amersham Co.) and treated for 4 hours at 65° C., and immersed into the mentioned buffer that contained heat-denatured $^{32}$p labeled DNA probe (2.5×10$^5$ cpm/ml) mentioned above at 65° C. overnight to allow hybridization. After the membrane was washed, the 3 clones that had OGF-II CDNA were able to be selected from about one million phages. The 3 clones were purified through two more screenings. After XL1-Blue MRF'cells, an *E. coli* strain, were infected with the purified phages, the infected cells were co-infected with helper phage ExAssist (prepared by Stratagene Co.). The supernatant cultivate was used to infect *E. coli* XLOLR (prepared by Stratagene Co.), and *E. coli* cells that became kanamycin resistant were obtained. The structure of plasmid DNA in one of these *E. coli* clones was analyzed and the nucleotide sequence of the inserted fragment was determined. The sequence is shown as SEQ ID NO:8. The amino-acid sequence deduced from SEQ ID NO:8 of OGF-II is shown as SEQ ID NO:9. Comparing this amino-acid sequence with wild type OGF-II amino-acid sequence, it is found that the former has one more Lys amino acid at the C-terminal (85th amino acid). Accordingly, the C-terminal lysine of bOGF-II purified form IMR-90 cells conditioned medium. Accordingly, the C-terminal lysine of bOGF-II purified from IMR-90 cells conditioned medium may have been cleaved off by (a) carboxypeptidase(s). This means that all of the 3 clones contained the DNA that coded an open reading frame consisting of 85 amino acids. from OGF-II N-terminal Glu-Thr-Glu-Tyr (SEQ ID NO:18). The open reading frame was determined from the position of the first termination codon and the amino acid sequence from the OGF-II protein. One of the obtained plasmid is named PBK-CMV OGF-II (3).

(2) Expression of OGF-II CDNA in *E. Coli*

The full length of OGF-II CDNA was amplified by PCR and isolated. The primers used were Q30F 5'-GGGGATCCGAGACAGAATATGGTC-3' (SEQ ID NO:19) and Q30R 5'-CCAAGCTTCTACTTGCTCTGCATACT-3'(SEQ ID NO:20). These primers were designed so that the amplified products can be digested with restriction enzymes BamHI and HindIII. Using the template of 20 ng of pBK-CMV OGF-II (3) and the primers (Q30F and Q30R), PCR was performed. The reaction solution contained 10 μl of 10×ExTaq buffer, 8 μl of 2.5 mM DNTP, 0.5 μl of Ex Taq, 9.5 μl of the DNA solution, 70 μl of distilled water, and 1 μl of the primer (100 μM each) in a final volume of 100 μl. After keeping the reaction mix at 95° C. for 3 minutes, 25 cycles of three-step incubation were performd that consisted of 95° C. for 3 minutes, 50° C. for 30 seconds, and 70° C. for 2 minutes. After these reactions the reaction mix was kept at 70° C. for 5 minutes. After the amplification, the primers were removed with Microcon 100 (Amicon Co.) and the PCR product was digested with restriction enzymes BamHI and HindIII; thereafter, the product was mixed with 20 ng of pOE30 (prepared by QIAGEN Co.) that was preliminarily cut with BamHI and HindIII and used for the ligation. Using the ligation solution, *E. coli* XL2-Blue (prepared by Stratagene Co.) was transformed. From the obtained ampicillin resistant colonies, a clone having the target insert fragment was separated by analyzing the DNA fragments digested with restriction enzymes and sequencing. The plasmid in this clone is named pQE30-OGF-II. The *E. coli* XL2-Blue (pQE30-OGF-II) having this plasmid has been deposited to NIBH, Agency of Industrial Science and Technology as "FERM BP-5139". The structure of plasmid contained in the deposited *E. coli* is shown FIG. 6. This strain was cultivated with shaking in super medium (2.5% bacto-tryptone, 1.5% bacto-yeast extract, 0.5% NaCl, 50 μg/ml ampicillin); when OD600 nm became 0.8, isopropyl β-D-thio-galatopylanoside (IPTG) was added at a final concentration of 0.5 mM, and the shaking cultivation was continued for another 20 hours to produce OGF-II with the *E. Coli*. After the cultivation finished, the strain was collected; the main band of molecular weight of about 15 KD was confirmed with SDS polyacrylamid gel electrophoresis. This molecular weight well coincided with that of the OGF-II that was obtained from cultured supernant of IMR90.

(3) Purification of His6-bOGF-II

To test the osteoblast growth activity of the protein obtained by translating bOGF-II gene, expression of the gene was performed using OIAexpress Kits (manufactured by QIAGEN Co.). In this system, protein containing histidine hexamer tag is produced, and purification is done using nickel-chelating nitrilotriacetic acid resin column that has high affinity to hIstidine hexamer tag. This system is generally used for efficiently purifying expressed protein. By using this system, bOGF-II is produced in the form having cluster of six histidines at the,N-terminal (His6-bOGF-II). To 0.35 g of *E. coli* treated with IPTG, 1.75 ml of 10 mM Tris-HC1, pH 8.0 that contains 8 M urea and 0.1 M sodium phosphate was added; agitated for one hour at room temperature. After the agitation, the sample was conttifuged at 12,000 rpm, for 15 minutes at room temperature and the supernant was collected. The supernant was added to 8 ml of 50% suspension of nickel-chelating nitrilotriacetic acid resin (manufactured by QIAGEN Co.) that was equilibrated with 10 mM Tris-HC1, 8 M urea, 0.1 M sodium phosphate, pH 8.0, the mixture was agitated for 45 minutes at room temperature. This resin was transferred into a column of 1.6 cm inside diameter and washed with 20 ml of 10 mM TrisHCl, 8 M urea, 0.1 M sodium phosphate, pH 8.0, at a flow rate of about 0.5 ml/min. Then, this column was further washed with 10 mM Tris-HCl, 8 M urea and 0.1 M sodium phosphate, pH 6.3, at a flow rate of about 0.5 ml/min. Finally, the target His6-bOGF-II was eluted with 10 mM Tris-HCl, 250 mM ‘midazole, 8 M urea, 0.1 M sodium phosphate, pH 6.3 at a flow rate of about 0.5 ml/min. The purified His6-bOGF-Il fraction was dialyzed for phosphate buffered saline.

(4) Osteoblast growth activity of His6-bOGF-II

The osteoblast growth activity of His6-bOGF-II was tested as described in Example 1 (2), method for testing ostsoblast growth activity. That is, the purified His6-bOGF-Il fraction described above was added to the assay medium, and incorporation of $^3$H-thymldine to mouse osteoblast MC3T3-El cells was tested.. The results are shown in FIG. 7. From these results, it has been confirmed that the protein produced by translating bOGF-II gene has the osteoblast growth activity as the wild type bOGF-II has.

Possibility for Use in Industry

According to the invention, a novel.protein with osteoblast growth activity and methods for producing the protein are provided. Since the protein of the instant invention has osteoblast growth activity, it is useful as a drug for the treatment of bone mass reduction such as osteoporosis and as antigen for immunological diagnosis of the diseases.

Reference to Microoraanisms deposited

Deposited Organization and Address that the Organisms were deposited:

National Institute of Bioscience and Human-Technology
Agency of Industrial Science and Technology
Ministry of International Trade and Industry 1–3, Higashi 1-chome, Tsukuba City, Ibaragi Prefecture Date of the Deposition to the Deposited Or ganimation:

Jun. 19, 1995

Deposit Number that the Deposited Organization provided:

FERM BP-5139

This deposit was transf erred from the national deposit (Acession Number: FERM P-14942 of May 26, 1995) on Jun. 19, 1995.

We claim:

1. A purified protein with an activity to stimulate osteoblast cell growth, having the amino acid sequence as set forth in SEQ ID NO: 9.

2. A purified protein with an activity to stimulate osteoblast cell growth, wherein the protein comprises the amino acid sequence as set forth in SEQ ID NO:9.

3. A method for producing a protein comprising: cultivating human fibroblasts; passing a conditioned medium thereof over a heparin column; eluting an adsorbed fraction; passing the eluant over an anion exchange column to obtain the non-adsorbed fraction; passing the non-adsorbed fraction over a cation exchange column; and further purifying with a heparin column to produce a protein that has the following characteristics:

(a) a molecular weight of about 15 kD under reducing and non-reducing conditions by sodium dodecyl sulfate—polyacrylamide gel electrophoresis (SDS-PAGE),
(b) a high affinity to a cation exchanger and heparin, and
(c) an activity to stimulate osteoblast cell growth that is decreased by heating at 70° C. for 10 minutes and inactivated by heating at 90° C for 10 minutes.

4. The method for producing a protein according to the claim 3, wherein the obtained protein comprises the amino acid sequence as set forth in SEQ ID NO:9, and has an activity to stimulate osteoblast cell growth.

5. A host cell which is transformed by an expression vector containing cDNA which encodes the amino acid sequence set forth in SEQ ID NO: 9, and which is *Escherichia coli* pQE30-OGF11 (Ferm BP-5139).

* * * * *

SEQUENCE LISTING (1) GENERAL INFORMATION:

(iii) NUMBER OF SEQUENCES:20

(2) INFORMATION FOR SEQ ID NO:1:

(i) SEQUENCE CHARACTERISTICS:
      (A) LENGTH: 25
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Glu Thr Glu Tyr Gly Pro Xaa Arg Arg Glu Met Glu Asp Thr Leu Asn
1               5                   10                  15

His Leu Lys Phe Leu Asn Val Leu Ser
            20                  25
```

(2) INFORMATION FOR SEQ ID NO:2:

(i) SEQUENCE CHARACTERISTICS:
      (A) LENGTH: 40
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Glu Thr Glu Tyr Gly Pro Cys Arg Arg Glu Met Glu Asp Thr Leu Asn
1               5                   10                  15

His Leu Lys Phe Leu Asn Val Leu Ser Pro Arg Gly Val Xaa Ile Pro
            20                  25                  30

Asn Cys Xaa Lys Lys Gly Phe Tyr
            35                  40
```

(2) INFORMATION FOR SEQ ID NO:3:

(i) SEQUENCE CHARACTERISTICS:
      (A) LENGTH: 9
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

```
Asp Val His Cys Tyr Ser Met Gln Ser
1               5
```

(2) INFORMATION FOR SEQ ID NO:4:

(i) SEQUENCE CHARACTERISTICS:
        (A) LENGTH: 12
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Glu Thr Glu Tyr Gly Pro Cys Arg Arg Glu Met Glu
1               5                   10
```

(2) INFORMATION FOR SEQ ID NO:5:

(i) SEQUENCE CHARACTERISTICS:
        (A) LENGTH: 16
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Asp Lys Tyr Gly Gln Pro Leu Pro Gly Tyr Thr Thr Lys Gly Lys Glu
1               5                   10                  15
```

(2) INFORMATION FOR SEQ ID NO:6:

(i) SEQUENCE CHARACTERISTICS:
        (A) LENGTH: 25
        (B) TYPE: amino acid
        (C) STRANDEDNESS: single
        (D) TOPOLOGY: linear (ii) MOLECULE TYPE: peptide (xi) SEQUENCE DESCRIPTION:SEQ ID NO:6:

```
Asp Lys Lys Gly Phe Tyr Lys Lys Lys Gln Cys Arg Pro Ser Lys Gly
1               5                   10                  15
Arg Lys Arg Gly Phe Cys Trp Cys Val
                20                  25
```

(2) INFORMATION FOR SEQ ID NO:7:

(i) SEQUENCE CHARACTERISTICS:
        (A) LENGTH: 22
        (B) TYPE: amino acid
        (C) STRANDEDNESS: single
        (D) TOPOLOGY: linear (xi) SEQUENCE DESCRIPTION: SEQ ID NO:7:

```
Asp Thr Leu Asn His Leu Lys Phe Leu Asn Val Leu Ser Pro Arg Gly
1               5                   10                  15

Val His Ile Pro Asn Cys
                20
```

(2) INFORMATION FOR SEQ ID NO:8:

(i) SEQUENCE CHARACTERISTICS:
        (A) LENGTH: 258
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: human (ix) FEATURE:
        (B) LOCATION: 1 to 258

(xi) SEQUENCE DESCRIPTION: SEQ ID NO:8:

GAGACAGAAT ATGGTCCCTG CCGTAGAGAA ATGGAAGACA CACTGAATCA CCTGAAGTTC    60

CTCAATGTGC TGAGTCCCAG GGGTGTACAC ATTCCCAACT GTGACAAGAA GGGATTTTAT   120

AAGAAAAAGC AGTGTCGCCC TTCCAAAGGC AGGAAGCGGG GCTTCTGCTG GTGTGTGGAT   180

AAGTATGGGC AGCCTCTCCC AGGCTACACC ACCAAGGGGA AGGAGGACGT GCACTGCTAC   240

AGCATGCAGA GCAAGTAG                                                 258

(2) INFORMATION FOR SEQ ID NO:9:

(i) SEQUENCE CHARACTERISTICS:
        (A) LENGTH: 85
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Glu Thr Glu Tyr Gly Pro Cys Arg Arg Glu Met Glu Asp Thr Leu Asn
1               5                   10                  15

His Leu Lys Phe Leu Asn Val Leu Ser Pro Arg Gly Val His Ile Pro
            20                  25                  30

Asn Cys Asp Lys Lys Gly Phe Tyr Lys Lys Gln Cys Arg Pro Ser
        35                  40                  45

Lys Gly Arg Lys Arg Gly Phe Cys Trp Cys Val Asp Lys Tyr Gly Gln
    50                  55                  60

Pro Leu Pro Gly Tyr Thr Thr Lys Gly Lys Glu Asp Val His Cys Tyr
65                  70                  75                  80

Ser Met Gln Ser Lys
            85

(2) INFORMATION FOR SEQ ID NO:10:

(i) SEQUENCE CHARACTERISTICS:
        (A) LENGTH: 7
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Glu Thr Glu Tyr Gly Pro Cys
1               5

(2) INFORMATION FOR SEQ ID NO:11:

(i) SEQUENCE CHARACTERISTICS:
        (A) LENGTH: 7
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Asp Lys Lys Gly Phe Tyr Lys
1               5

(2) INFORMATION FOR SEQ ID NO:12:

(i) SEQUENCE CHARACTERISTICS:
        (A) LENGTH: 4
        (B) TYPE: amino acid
        (C) STRANDEDNESS: single
        (D) TOPOLOGY: linear (ii) MOLECULE TYPE: peptide (xi) SEQUENCE DESCRIPTION:SEQ ID NO:12:

Glu Thr Glu Tyr (2) INFORMATION FOR SEQ ID NO:13:

(i) SEQUENCE CHARACTERISTICS:
        (A) LENGTH: 24 base pair
        (B) TYPE: nucleic acid
        (C) STRANDEDNESS: single
        (D) TOPOLOGY: linear (ii) MOLECULE TYPE: genomic DNA (xi) SEQUENCE DESCRIPTION:SEQ ID NO:13:

GGGGATCCGA GACAGAATAT GGTC                                          24

(2) INFORMATION FOR SEQ ID NO:14:

(i) SEQUENCE CHARACTERISTICS:
        (A) LENGTH: 26 base pair
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO:14:

CCAAGCTTCT ACTTGCTCTG CATACT                                        26

(2) INFORMATION FOR SEQ ID NO:15:

(i) SEQUENCE CHARACTERISTICS:
        (A) LENGTH: 7
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Glu Thr Glu Tyr Gly Pro Cys
  1               5

(2) INFORMATION FOR SEQ ID NO:16:

(i) SEQUENCE CHARACTERISTICS:
        (A) LENGTH: 20 base pair
        (B) TYPE: nucleic acid
        (C) STRANDEDNESS: single
        (D) TOPOLOGY: linear (ii) MOLECULE TYPE: genomic DNA (xi) SEQUENCE DESCRIPTION:SEQ ID NO:16:

AGRACNGART AYGGNCCNTG                                               20

(2) INFORMATION FOR SEQ ID NO:17:

-continued

```
        (i) SEQUENCE CHARACTERISTICS:
            (A) LENGTH: 7
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:17:

Asp Lys Lys Gly Phe Tyr Lys
 1               5

(2) INFORMATION FOR SEQ ID NO:18:

(i) SEQUENCE CHARACTERISTICS:
            (A) LENGTH: 20 base pair
            (B) TYPE: nucleic acid
            (C) STRANDEDNESS: single
            (D) TOPOLOGY: linear (ii) MOLECULE TYPE: genomic DNA (xi) SEQUENCE DESCRIPTION: SEQ ID NO:18:

TTRTARAANC CYTTYTTRTC                                                    20

(2) INFORMATION FOR SEQ ID NO:19:

(i) SEQUENCE CHARACTERISTICS:
            (A) LENGTH: 24 base pair
            (B) TYPE: nucleic acid
            (C) STRANDEDNESS: single
            (D) TOPOLOGY: linear (ii) MOLECULE TYPE: genomic DNA (xi) SEQUENCE DESCRIPTION: SEQ ID NO:19:

GGGGATCCGA GACAGAATAT GGTC                                               24

(2) INFORMATION FOR SEQ ID NO:20:

(i) SEQUENCE CHARACTERISTICS:
            (A) LENGTH: 26 base pair
            (B) TYPE: nucleic acid
            (C) STRANDEDNESS: single
            (D) TOPOLOGY: linear (ii) MOLECULE TYPE: genomic DNA (xi) SEQUENCE DESCRIPTION: SEQ ID NO:20:

CCAAGCTTCT ACTTGCTCTG CATACT                                             26
```